United States Patent [19]
Pullen et al.

[11] Patent Number: 5,753,593
[45] Date of Patent: May 19, 1998

[54] CONTROL OF AQUATIC VEGETATION WITH SURFACTANT AND TERPENE OIL

[76] Inventors: Erroll M. Pullen; Melvin D. Pullen, both of 3255 Burnt Mill Dr., Wilmington, N.C. 28403

[21] Appl. No.: 575,341

[22] Filed: Dec. 20, 1995

[51] Int. Cl.$^6$ .......................... A01N 25/30; A01N 31/04; A01N 61/02
[52] U.S. Cl. .............................................. 504/150; 504/161
[58] Field of Search ...................................... 504/150, 161

[56] References Cited

U.S. PATENT DOCUMENTS

| | | | |
|---|---|---|---|
| 4,039,588 | 8/1977 | Wilson et al. | 260/613 R |
| 5,330,671 | 7/1994 | Pullen et al. | 252/88 |
| 5,444,078 | 8/1995 | Yu et al. | 514/372 |
| 5,527,482 | 6/1996 | Pullen et al. | 252/88 |

*Primary Examiner*—S. Mark Clardy
*Attorney, Agent, or Firm*—Arthur W. Fisher, III

[57] ABSTRACT

An environmentally compatible aquatic herbicidal composition comprising at least one surfactant and at least one high terpene containing natural oil to effectively control target aquatic vegetation including Red Azolla, Salvinia Molesta and Lemna.

5 Claims, No Drawings

CONTROL OF AQUATIC VEGETATION WITH SURFACTANT AND TERPENE OIL

BACKGROUND OF THE INVENTION

1. Field of the Invention

An environmentally compatible aquatic herbicide to effectively control target aquatic vegetation such as Red Azolla, Salvinia Molesta and Lemna.

2. Description of the Prior Art

Aquatic and wetland vegetation such as Red Azolla, Salvinia Molesta and Lemna have caused detrimental effects on ponds, lakes, rivers and streams throughout the United States and elsewhere. When present in high density, these weeds can literally choke these bodies of water restricting access by boats and disrupting drainage, irrigation, flood control and water conservation projects and hydroelectric power plants. In addition, such bodies of water create an environment for disease carrying mosquitoes and snails, eliminate fishing in certain areas, and alter aquatic ecosystems by preventing sunlight from reaching other plants and animals. The reduction of such vegetation must be controlled.

Aquatic and wetland weeds have been controlled mechanically by machinery, biologically by a variety of insects, pathogens, and other organisms and chemically through the use of chemical herbicides.

U.S. Pat. No. 5,407,899 teaches a combination of surfactant carrier mixture with an aqueous copper complex in emulsified form providing rapid algaecidal and herbicidal action. This mixture includes alkwv sulfonate, alkyl sulfate and limonene.

U.S. Pat. No. 5,096,468 shows an environmentally compatible herbicidal conposition comprising a fatty acid active ingredient, an oil component and an emulsifier component. The composition is a foliar applied herbicide which effectively controls a variety of unwanted wood and grass species. The fatty acid component of the herbicidal composition comprises pelargonic acid which may be used alone or as the predominant component of a mixture of fatty acids including caprylic, pelargonic, capric, undecanoic and louric acids. The oil component comprises a triglyceride (various vegetable oils), a terpenoid-based oil or a paraffinic mineral oil. The emulsifier component comprises one or more anionic or nonionic emulsifiers.

U.S. Pat. No. 4,983,389 teaches super absorbent solid organic polymers which absorb over 100 times their weight in water used in aquatic and wetland environment plant (weed) population control compositions. Methods for using the solid or flowable, super absorbent polymer herbicidal delivery agents for the control of aquatic and wetland plant populations, or for the simultaneous or concurrent control of both aquatic plant and aquatic insect (particularly mosquitoes) populations, in an area needing aquatic wetland environment plant (weed) control treatment.

U.S. Pat. No. 5,403,587 shows an aqueous antimicrobial composition containing one or more essential oils which exhibit antimicrobial properties and which can be combined with a water carrier and a solubilizing or dispersing agent to form a solution or a dispersion of the essential oil in the water carrier, the essential oil exhibiting antimicrobial properties when incorporated in the water carrier.

Additional examples of the prior art are found in U.S. Pat. No. 5,087,353 and U.S. Pat. No. 5,389,257.

SUMMARY OF THE INVENTION

The present invention relates to an environmentally compatible aquatic herbicidal composition comprising at least one surfactant and at least one high terpine containing natural oil to effectively control target aquatic vegetation including Red Azolla, Salvinia Malesta and Lemna.

High terpine containing natural oil as used herein means those natural oils having a terpine content of at least fifty (50%) percent. It is preferable that the high terpine natural oil contains at least ninety (90%) percent. Suitable high terpine containing natural oils includes oil from conifers such as citrus peel oils, preferably orange oil, grapefruit oil and lemon oil; or pine oil. Of these, orange oil is the most preferred. Naturally, the amount of high terpene containing natural oils in the aquatic herbicidal composition will depend upon the amount of terpenes in the specific oil used.

The aquatic herbicidal composition of the instant invention further contains at least one surfactant. Generally, conventional surfactants such as anionic and nonionic surfactants are acceptable. Preferred are anionic surfactants such as salts of fatty acids, alkyl sulphates, alkyl ether sulphonates and alkyl aryl sulphonates. Examples of preferred surfactants include sodium dodecylbenzene sulphonate, sodium lauryl ether sulphate and salts such as sodium salts of secondary alkane sulphonates.

Examples of more preferable surfactants include sodium alkyl ethoxy sulphate, linear alcohol exthoxylate such as lauryl alcohol ethoxylate, alkane sulphonate and alkyl sulphonic acid.

The aquatic herbicidal composition may also contain various additives such as antioxidant, preservatives, pH neutralizers and/or clarifiers.

Since the aquatic herbicidal composition is an aqueous composition, the balance of the aquatic herbicidal composition is water.

In use, the aquatic herbicidal composition is sprayed directly to the surface of the target aquatic vegetation at a dilution rate of 100 to 1 by weight with water. The aquatic herbicidal composition reduces the surface tension of water causing the target aquatic vegetation to sink. The aquatic herbicidal composition also assists in the process by removing the wax substance on the aquatic vegetation allowing the aquatic herbicidal composition to more efficiently wet the leaves. In some cases, a second application may be required.

When so applied, the aquatic herbicidal composition has been effective in controlling Red Azolla, Salvinia Molesta and Lemna.

DETAILED DESCRIPTION OF THE PREFERRED EMBODIMENT

The present invention relates to an environmentally compatible aquatic herbicidal composition comprising at least one surfactant and at least one high terpine containing natural oil to effectively control target aquatic vegetation including Red Azolla, Salvinia Malesta and Lemna.

High terpine containing natural oil as used herein means those natural oils having a terpine content of at least fifty (50%) percent. It is preferable that the high terpine natural oil contains at least ninety (90%) percent. Suitable high terpine containing natural oils includes oil from conifers such as citrus peel oils, preferably orange oil, grapefruit oil and lemon oil; or pine oil. Of these, orange oil is the most preferred.

Naturally, the amount of high terpene containing natural oils in the aquatic herbicidal composition will depend upon the amount of terpenes in the specific oil used. Generally, the aquatic herbicidal composition will contain from about 1% to about 15% by weight of high terpine containing natural oil, preferably from about 4% to about 10% by weight and more preferably from about 5% to about 7% by weight.

While not to be bound by theory, it is believed that the terpenes in the natural oils provide the mechanism for obtaining the objects of the invention. For example, the terpenes are believed to break up the wax protective cover coating the target aquatic vegetation which together with the reduction of the surface tension of the water cause the target aquatic vegetation to rapidly sink beneath the surface of the water and ultimately to the bottom. Further, since the high terpene containing oils are natural oils, the aquatic herbicidal composition is environmentally acceptable thereby avoiding water contamination and pollution.

The aquatic herbicidal composition of the instant invention further contains at least one surfactant. Generally, conventional surfactants such as anionic and nonionic surfactants are acceptable. Preferred are anionic surfactants such as salts of fatty acids, alkyl sulphates, alkyl ether sulphonates and alkyl aryl sulphonates. Examples of preferred surfactants include sodium dodecylbenzene sulphonate, sodium lauryl ether sulphate and salts such as sodium salts of secondary alkane sulphonates (e.g., Hostaspun SAS 60 marketed by Hoechst).

Also, ethoxylated nonylphenols with 8–10 moles of ethylene oxide and ethoxylated octylphenols with 8–10 moles of ethylene oxide (e.g., alkyl polyglycol ether N9) may be used in the aquatic herbicidal composition.

Examples of more preferable surfactants include sodium alkyl ethoxy sulphate, linear alcohol exthoxylate such as lauryl alcohol ethoxylate, alkane sulphonate and alkyl sulphonic acid.

Generally, the aquatic herbicidal composition will contain from about 10% to about 40% by weight of surfactant(s), preferably from about 15% to about 25% by weight and more preferably from about 20% to about 22% by weight.

The aquatic herbicidal composition may also contain various additives such as antioxidant, preservatives, pH neutralizers and/or clarifiers.

An example of a suitable antioxidant is BHT (2,6-di-tert-butyl-paracresol). The antioxidant(s) added to the aquatic herbicidal composition may range of from about 0.01% to about 1% by weight, preferably from about 0.08% to about 0.12% by weight and more preferably about 0.10% by weight.

Examples of suitable preservatives include phenonip, 2-brom-02-nitropropane-1, 3 diol, formaldehyde, methylparaben, propylparaben, borax and/or mixtures thereof. The preservatives may be added to the aquatic herbicidal composition in an amount from about 0.1% to about 5% by weight, preferably from about 0.2% to about 0.6% by weight and more preferably about 0.4% by weight.

Caustic crystals may be added in an amount from about 1.0% to about 1.5% by weight and more preferably about 1.2% by weight to clarify the aquatic herbicidal composition.

An example of a suitable pH neutralizer is urea in an amount from about 0.5% to about 1.5% by weight and more preferably about 1.0% by weight.

Since the aquatic herbicidal composition is an aqueous composition, the balance of the aquatic herbicidal composition is up to about 70% of water by weight.

An example of an effective aquatic herbicidal composition comprises about 11% sodium dodecyl benzene sulphonate, about 5% sodium lauryl ether sulphate, about 9% cold pressed orange oil, about 3.5% alkyl aryl polyglycolether N9, and about 1.4% of the sodium salt of a secondary alkane sulphonate with the balance of water (all percentages are by weight). A preservative comprising about 1.0% by weight of formaldehyde and an antioxidant such as BHT of about 0.1% by weight may also be added.

The preferred aquatic herbicidal composition comprises about 5.52% of cold pressed orange oil, about 6.26% of sodium alkyl ethoxy sulphate, about 4.60 % of lauryl alcohol ethoxylate, about 1.20% of alkane sulphonate, about 9.75 alkyl sulphonic acid and about 70.26% water, all by weight.

In addition, about 0.09% of BHT antioxidant cao-3 2, 6-kl tert butyl-p-cresol, about 0.10% of 2-brom-02-nitropropane-1, 3 diol, about 1.02% of urea, and about 1.20% of caustic crystals, all by weight, may be added.

In use, the aquatic herbicidal composition is sprayed directly to the surface of the target aquatic vegetation at a dilution rate of 100 to 1 by weight with water. The aquatic herbicidal composition reduces the surface tension of water causing the weeds to sink. The aquatic herbicidal composition also assists in the process by removing the wax substance on the aquatic vegetation allowing the aquatic herbicidal composition to more efficiently wet the leaves. In some cases, multiple applications may be required.

When so applied, the aquatic herbicidal composition has been effective in controlling Red Azolla, Salvinia Molesta and Lemna as indicated by the test results indicating the target aquatic vegetation density following application of the aquatic herbicidal composition.

| Test 1 | Day 0 | Day 3 | Day 7 2nd appl. | Day 10 |
| --- | --- | --- | --- | --- |
| Azolla | 95% | 60% | 40% | 0% |
| Salvinia | 5% | 2% | 1% | 0% |

| Test 2 | Day 0 | Day 3 | Day 7 2nd appl. | Day 10 |
| --- | --- | --- | --- | --- |
| Azolla | 60% | 30% | 15% | 5% |
| Salvinia | 10% | 5% | 2% | 1% |
| Lemna | 20% | 10% | 15% | 2% |

| Test 3 | Day 0 | Day 7 2nd appl. | Day 10 | Day 15 |
| --- | --- | --- | --- | --- |
| Salvinia | 45% | 35% | 20% | 5% |

| Test 4 | Day 0 | Day 2 | Day 9 2nd appl. | Day 11 3rd appl. | Day 12 |
| --- | --- | --- | --- | --- | --- |
| Lemna | 98% | 70% | 90% | 50% | 15% |
| Azolla | 5% | 2% | 2% | 0% | 0% |

While the invention has been described above with respect to certain particular embodiments thereof, numerous other forms and modifications will be apparent to those skilled in the art. The appended claims and the invention generally should be construed as covering all such obvious forms and modifications which are within the true spirit and scope of the invention.

What is claimed is:

1. A method of controlling aquatic vegetation floating in a body of water comprising the following steps:

a) applying a composition consisting essentially of at least one surfactant selected from sodium alkyl ethoxy sulphate, linear alcohol, ethoxylate, alkane sulphonate and alkyl sulphonic acid, or mixtures thereof and at least one high terpene containing natural oil selected from citrus peel oils, pine oils or mixtures thereof to the surface of the floating aquatic vegetation;

b) allowing the composition to penetrate the protective coating on the leaves of the floating aquatic vegetation; and c) allowing the floating aquatic vegetation to become saturated causing the aquatic vegetation to sink.

2. The method of controlling aquatic vegetation floating in a body of water of claim 1 containing from about 10% to about 40% of said surfactant(s) by weight and from about 1% to about 15% of said high terpene containing natural oil(s) by weight.

3. The method of controlling aquatic vegetation floating in a body of water of claim 1 containing from about 15% to about 25% of said surfactant(s) by weight and from about 4% to about 10% of said high terpene containing natural oil(s) by weight.

4. The method of controlling aquatic vegetation floating in a body of water of claim 1 comprising about 5.52% of cold pressed orange oil, about 6.26% of sodium alkyl ethoxy sulphate, about 4.60% of lauryl alcohol ethoxylate, about 1.20% of alkane sulphonate, about 9.75% alkyl sulphonic acid and about 70.26% water, all by weight.

5. The method of controlling aquatic vegetation floating in a body of water of claim 4 further comprising 0.09% of BHT antioxidant cao-3 2, 6-di tert butyl-p-cresol, about 0.10% of 2-bromo-2-nitropropane-1, 3-diol, about 1.02% of urea, and about 1.20% of caustic crystals, all by weight.

* * * * *